United States Patent
Dittmer et al.

(10) Patent No.: US 10,590,028 B2
(45) Date of Patent: Mar. 17, 2020

(54) LITHIUM SILICATE-WOLLASTONITE GLASS CERAMIC

(71) Applicant: Ivoclar Vivadent AG, Schaan (LI)

(72) Inventors: Marc Dittmer, Feldkirch (AT); Wolfram Höland, Schaan (LI); Markus Rampf, Lachen (CH); Marcel Schweiger, Chur (CH)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 15/754,176

(22) PCT Filed: Sep. 2, 2016

(86) PCT No.: PCT/EP2016/070740
§ 371 (c)(1),
(2) Date: Feb. 21, 2018

(87) PCT Pub. No.: WO2017/055010
PCT Pub. Date: Apr. 6, 2017

(65) Prior Publication Data
US 2018/0244563 A1    Aug. 30, 2018

(30) Foreign Application Priority Data
Sep. 30, 2015  (EP) .................................. 15187666

(51) Int. Cl.
| | | |
|---|---|---|
| *C03C 10/00* | (2006.01) | |
| *C03C 3/097* | (2006.01) | |
| *A61L 27/10* | (2006.01) | |
| *C03C 4/00* | (2006.01) | |
| *A61K 6/02* | (2006.01) | |

(52) U.S. Cl.
CPC .......... *C03C 10/0009* (2013.01); *A61K 6/024* (2013.01); *A61K 6/025* (2013.01); *A61K 6/0215* (2013.01); *A61K 6/0235* (2013.01); *A61K 6/0255* (2013.01); *A61L 27/10* (2013.01); *C03C 3/097* (2013.01); *C03C 4/0021* (2013.01); *C03C 10/0027* (2013.01); *A61L 2430/12* (2013.01)

(58) Field of Classification Search
CPC .. C03C 10/00; C03C 10/0009; C03C 10/0027
See application file for complete search history.

(56) References Cited

U.S. PATENT DOCUMENTS

| | | | |
|---|---|---|---|
| 4,515,634 A | 5/1985 | Wu et al. | |
| 5,219,799 A | * 6/1993 | Beall ................... | C03C 10/0009 501/5 |
| 5,356,436 A | 10/1994 | Nonami et al. | |
| 5,711,763 A | 1/1998 | Nonami et al. | |
| 8,047,021 B2 | 11/2011 | Schweiger et al. | |
| 2005/0079226 A1 | 4/2005 | Gonda et al. | |

FOREIGN PATENT DOCUMENTS

| | | | |
|---|---|---|---|
| DE | 247574 A3 | 7/1987 | |
| DE | 262366 A1 | 11/1988 | |
| GB | 2224025 A * | 4/1990 | ......... C03C 10/0009 |
| GB | 2224025 A | 4/1990 | |
| WO | 0234685 A1 | 5/2002 | |

OTHER PUBLICATIONS

International Preliminary Report on Patentability of PCT/EP2016/070740, Apr. 3, 2018, 7 pages.

Höland, Wolfram et al., "Glass Ceramic Technology," The American Ceramic Society, Second Edition, pp. 114-116, 2012, Wiley, USA.

Dittmer, Marc, "Glasses and glass-ceramics in the system of MgO-Al2O3-SiO2 with ZrO2 as nucleating agent," Dissertation of Dr. Marc Dittmer, University of Jena, Germany, 2011.

Salman, S. et al., "Crystallization Behavious of Some Glasses in the System LiO2-CaO-MgO-SiO2," Sprechsaal Bd., vol. 118, No. 9, pp. 782-788, 1985.

* cited by examiner

*Primary Examiner* — Noah S Wiese
(74) *Attorney, Agent, or Firm* — Ann M. Knab; Thad McMurray

(57) ABSTRACT

Lithium silicate-wollastonite glass ceramics are described which are characterized by a controllable translucence and can be easily machined and therefore can be used in particular as restoration material in dentistry.

22 Claims, No Drawings

LITHIUM SILICATE-WOLLASTONITE GLASS CERAMIC

CROSS-REFERENCE TO RELATED APPLICATIONS

This application is a National Stage application of International patent application PCT/EP2016/070740 filed on Sep. 2, 2016, which claims priority to European patent application No. 15187666.1 filed on Sep. 30, 2015, all the disclosures of which are incorporated herein by reference in their entirety.

FIELD OF THE INVENTION

The invention relates to lithium silicate-wollastonite glass ceramic which is suitable in particular for use in dentistry, preferably for the preparation of dental restorations, as well as to precursors for the preparation of the glass ceramic.

BACKGROUND OF THE INVENTION

Glass ceramics with a lithium silicate crystal phase and the use thereof in dental products are known from the state of the art. For example, PP 1 505 041 describes lithium silicate glass ceramics which, in the form of lithium metasilicate glass ceramics, are processed by means of CAD/CAM processes to form the desired dental restorations, wherein a subsequent heat treatment leads to the conversion of the lithium metasilicate ($Li_2SiO_3$) phase into lithium disilicate ($Li_2Si_2O_5$) phase and thus to the formation of high-strength lithium disilicate glass ceramic. Machining of the glass ceramic after the formation of the lithium disilicate phase is, in particular because of the high strength thereof, time-consuming and associated with high tool wear.

Glass ceramics which contain wollastonite as crystal phase are also known.

Wollastonite glass ceramics are primarily used as façade materials in the construction industry (cf. Höland, Beall, "Glass-Ceramic Technology", Wiley, USA, $2^{nd}$ Edition, 2012, pp. 114-116).

DD 247 574 describes glass ceramics with apatite and wollastonite as crystal phases. The glass ceramics are used for bone replacement and their high bioactivity means that they can form a firm bond to the bone in the living organism.

DD 262 366 discloses restorative tooth materials made of glass ceramics, which contain apatite and moreover wollastonite, as well as optionally perovskite, cristobalite and/or sphene as crystal phases.

DE 692 04 791 describes glass ceramics, which are used to produce tableware. The glass ceramics comprise, as predominant crystal phase, lithium disilicate, as well as small proportions of spodumene, cristobalite and wollastonite.

US 2005/0079226 describes bioactive glasses, which are used as sintering aid in materials for replacing bone. After crystallization, the glasses comprise wollastonite and diopside as crystal phases.

Bioactive ceramics are known from U.S. Pat. No. 5,356,436, which serve to replace bones and which, on contact with body fluids, can form for example hydroxyapatite on their surface. The ceramics can have e.g. diopside, wollastonite, alite, belite, akermanite, monticellite, forsterite, protoenstatite and tridymite as crystal phases.

U.S. Pat. No. 5,711,763 describes bioactive implants made of a metallic substrate, in the surface of which ceramic particles are embedded. The ceramic materials can originate for example from the group consisting of diopside, wollastonite, alite, belite, akermanite, monticellite, forsterite, protoenstatite and tridymite.

However, the known glass ceramics have a number of disadvantages. With these, in many cases the translucence cannot be adjusted over a broad range as is desirable for dental materials which can be used for many purposes. Moreover, with these, simple machining is often not possible. In addition, their strength often proves not to be sufficient to allow them to be used as restorative dental material.

SUMMARY OF THE INVENTION

The object of the invention is to provide a glass ceramic which has good optical properties, in particular a controllable translucence, as well as good mechanical properties and thus can be used as a restorative dental material. The glass ceramic snail, moreover, be simply and quickly processable using machining, e.g. by means of CAD/CAM processes, to form dental restorations. This simple processing shall, in particular, also be possible after the desired crystal phases have crystallized as completely as possible.

This object is achieved by the lithium silicate-wollastonite glass ceramic according to the attached claims. Also a subject of the invention are the starting glass according to the attached claims, the process according to the attached claims, as well as the method of use according to attached claims.

DETAILED DESCRIPTION

The lithium silicate-wollastonite glass ceramic according to the invention is characterized in that it comprises lithium silicate as a crystal phase and wollastonite as a further crystal phase.

This glass ceramic surprisingly displays an advantageous combination of mechanical and optical properties desirable for a restorative dental material, and it can also be given the desired shape, for example of a dental restoration such as a crown, in a manner advantageous for a dental material.

The glass ceramic according to the invention comprises 55.0 to 74.0, in particular 56.0 to 73.0 and preferably 60.0 to 69.0 wt.-% $SiO_2$.

It is further preferred that the glass ceramic comprises 10.0 to 18.0, in particular 11.0 to 17.0 and preferably 12.0 to 16.5 wt.-% $Li_2O$.

It is furthermore preferred that the glass ceramic comprises 4.0 to 17.0, in particular 5.0 to 16.0 and preferably 7.0 to 15.0 wt.-% CaO.

The glass ceramic preferably comprises 0.5 to 6.0, in particular 0.5 to 5.0 and preferably 1.0 to 4.0 wt.-% $Al_2O_3$.

It is further preferred that the glass ceramic comprises 0 to 5.0, in particular 0 to 4.5 and preferably 0.5 to 4.0 wt.-% $K_2O$.

A glass ceramic is further preferred which comprises 1.0 to 7.0, in particular 2.0 to 6.0 and preferably 3.0 to 6.0 wt.-% $P_2O_5$. $P_2O_5$ can in particular act as nucleating agent for the formation of lithium silicate. The presence of a nucleating agent is, however, not absolutely necessary for the formation of lithium silicate as crystal phase.

It is also preferred that the glass ceramic, in addition to $Li_2O$ and $K_2O$, comprises further alkali metal oxide $Me^I_2O$ in an amount of 0 to 13.0, preferably 0 to 12.0 and particularly preferably 0 to 11.0 wt.-%, wherein $Me^I_2O$ is selected from $Na_2O$, $Rb_2O$ and/or $Cs_2O$.

The glass ceramic particularly preferably comprises at least one and in particular all of the following further alkali metal oxides $Me^I_2O$ in the amounts specified:

| Component | wt.-% |
|---|---|
| $Na_2O$ | 0 to 7.0, in particular 0 to 6.0 |
| $Rb_2O$ | 0 to 11.0, in particular 0 to 8.0 |
| $Cs_2O$ | 0 to 13.0, in particular 0 to 12.0 |

In addition, it is preferred that the glass ceramic comprises 0 to 6.0 and preferably 0 to 5.0 wt.-% further oxide of divalent elements $Me^{II}O$, wherein $Me^{II}O$ is selected from MgO, SrO and/or ZnO.

The glass ceramic particularly preferably comprises at least one and in particular all of the following oxides of divalent elements $Me^{II}O$ in the amounts specified:

| Component | wt.-% |
|---|---|
| MgO | 0 to 3.0, in particular 0 to 2.0 |
| SrO | 0 to 6.0, in particular 0 to 5.0 |
| ZnO | 0 to 5.0, in particular 0 to 4.0 |

A glass ceramic is further preferred which comprises 0 to 6.0 and preferably 0 to 5.0 wt.-% oxide of trivalent elements $Me^{III}_2O_3$, wherein $Me^{III}_2O_3$ is selected from $B_2O_3$, $Y_2O_3$, $La_2O_3$, and/or $Er_2O_3$. The glass ceramic particularly preferably comprises at least one and in particular all of the following oxides of trivalent elements $Me^{III}_2O_3$ in the amounts specified:

| Component | wt.-% |
|---|---|
| $B_2O_3$ | 0 to 4.0, in particular 0 to 3.5 |
| $Y_2O_3$ | 0 to 5.0, in particular 0 to 4.0 |
| $La_2O_3$ | 0 to 6.0, in particular 0 to 5.0 |
| $Er_2O_3$ | 0 to 2.0, in particular 0 to 1.0 |

A glass ceramic is further preferred which comprises 0 to 8.0 and preferably 0 to 7.0 wt.-% further oxide of tetravalent elements $Me^{IV}O_2$, wherein $Me^{IV}O_2$ is selected from $ZrO_2$, $GeO_2$, $CeO_2$, $TiO_2$ and/or $SnO_2$.

The glass ceramic particularly preferably comprises at least one and in particular all of the following further oxides of tetravalent elements $Me^{IV}O_2$ in the amounts specified:

| Component | wt.-% |
|---|---|
| $ZrO_2$ | 0 to 7.0, in particular 0 to 6.0 |
| $GeO_2$ | 0 to 6.0, in particular 0 to 5.0 |
| $CeO_2$ | 0 to 3.0, in particular 0 to 2.0 |
| $TiO_2$ | 0 to 5.0, in particular 0 to 4.0 |
| $SnO_2$ | 0 to 8.0, in particular 0 to 7.0 |

A glass ceramic is also preferred which comprises 0 to 6.0 and preferably 0 to 5.0 wt.-% further oxide of pentavalent elements $Me^V_2O_5$, wherein $Me^V_2O_5$ is selected from $V_2O_5$, $Ta_2O_5$ and/or $Nb_2O_5$.

The glass ceramic particularly preferably comprises at least one and in particular all of the following further oxides of pentavalent elements $Me^V_2O_5$ in the amounts specified:

| Component | wt.-% |
|---|---|
| $V_2O_5$ | 0 to 5.0, in particular 0 to 4.0 |
| $Ta_2O_5$ | 0 to 5.0, in particular 0 to 4.0 |
| $Nb_2O_5$ | 0 to 6.0, in particular 0 to 5.0 |

A glass ceramic is also preferred which comprises 0 to 6.0 wt.-% oxide of hexavalent elements $Me^{VI}O_3$, wherein $Me^{VI}O_3$ is selected from $WO_3$ and/or $MoO_3$.

The glass ceramic particularly preferably comprises at least one and in particular all of the following oxides $Me^{VI}O_3$ in the amounts specified:

| Component | wt.-% |
|---|---|
| $WO_3$ | 0 to 6.0, in particular 0 to 5.0 |
| $MoO_3$ | 0 to 4.0, in particular 0 to 3.0 |

A glass ceramic is particularly preferred which comprises at least one and preferably all of the following components in the amounts specified:

| Component | wt.-% |
|---|---|
| $SiO_2$ | 56.0 to 74.0 |
| $Li_2O$ | 10.0 to 18.0 |
| CaO | 4.0 to 17.0 |
| $Al_2O_3$ | 0.5 to 6.0 |
| $K_2O$ | 0 to 5.0 |
| $P_2O_5$ | 1.0 to 7.0 |
| $Me^I_2O$ | 0 to 13.0 |
| $Me^{II}O$ | 0 to 6.0 |
| $Me^{III}_2O_3$ | 0 to 6.0 |
| $Me^{IV}O_2$ | 0 to 8.0 |
| $Me^V_2O_5$ | 0 to 6.0 |
| $Me^{VI}O_3$ | 0 to 6.0, | wherein $Me^I_2O$, $Me^{II}O$, $M^{III}_2O_3$, $Me^{IV}O_2$, $Me^V_2O_5$ and $Me^{VI}O_3$ have the above-specified meaning.

Some of the above-named components can serve as colorants and/or fluorescent agents. The glass ceramic according to the invention can in addition also comprise further colorants and/or fluorescent agents, which can be selected in particular from inorganic pigments and/or oxides of d-block and f-block elements, such as the oxides of Sc, Mn, Fe, Co, Pr, Nd, Tb, Dy, Gd, Eu and Yb. Metal colloids, e.g. of Ag, Au and Pd, which can in addition also act as nucleating agents, can also be used as further colorants. These metal colloids can be formed e.g. by reduction of corresponding oxides, chlorides or nitrates during the melting and crystallization processes.

The properties of the glass ceramic are substantially influenced by the crystal phases. The glass ceramic according to the invention comprises lithium silicate as a crystal phase. The term "lithium silicate" denotes at least one crystal phase selected from lithium disilicate and lithium metasilicate. Consequently, the glass ceramic according to the invention comprises lithium disilicate, lithium metasilicate or a mixture of lithium disilicate and lithium metasilicate as crystal phase.

In a preferred embodiment, the glass ceramic according to the invention comprises lithium metasilicate or lithium disilicate as main crystal phase and in particular lithium disilicate as main crystal phase.

The term "main crystal phase" denotes the crystal phase which has the highest proportion by mass of all the crystal phases present in the glass ceramic. The masses of the crystal phases are determined in particular by means of the Rietveld method. A suitable process for the quantitative analysis of the crystal phases using the Rietveld method is described e.g. in M. Dittmer's doctoral thesis "Gläser und Glaskeramiken im System MgO—$Al_2O_3$—$SiO_2$ mit $ZrO_2$ als Keimbildner" [Glasses and glass ceramics in the MgO—$Al_2O_3$—$SiO_2$ system with $ZrO_2$ as nucleating agent], University of Jena 2011.

The glass ceramic according to the invention also comprises, in addition to lithium silicate as crystal phase, wollastonite, $CaSiO_3$, as further crystal phase.

The glass ceramic according to the invention can in addition comprise further crystal phases, such as for example $Li_3PO_4$, $SiO_2$, $LiAlSi_2O_6$, $CsAlSi_5O_{12}$, scheelite, $Li_xAl_xSi_{1-x}O_2$ and/or $LiAlSi_3O_8$. It is preferred that the glass ceramic comprises $Li_3PO_4$ as further crystal phase.

The type and amount of crystal phases formed can be controlled in particular by the composition of the starting glass as well as the process for the preparation of the glass ceramic. The examples illustrate this by means of the variation of the composition and the preparation process.

It was surprisingly found that a glass ceramic can be provided which, in addition to a wollastonite crystal phase, also has a lithium silicate crystal phase. In particular it was not foreseeable that such a glass ceramic can be formed in the preferred composition range described above. It was found that the nucleation and the growth of both crystal phases obviously proceed alongside one another in the starting glass. Lithium silicate crystals were detectable in the volume of the starting glass, while wollastonite crystals were detectable on the surface of the starting glass. Accordingly, nucleation and growth of lithium silicate crystals seem to occur in the volume of the starting glass and, in contrast, nucleation and growth of wollastonite crystals seem to occur on the surface of the starting glass. Among experts, crystallization in the volume of a glass is also called volume crystallization and crystallization on the surface is also called surface crystallization.

However, the nucleation and crystallization on the surface does not take place readily during the preparation of the glass ceramic according to the invention. Rather it was found that it is necessary to activate the surface of the starting glass by grinding it. By means of this specific activation a reproducible surface crystallization of wollastonite is achieved. The manner of grinding, for example the use of different mills, can influence the amount of finally crystallized wollastonite.

The amount of wollastonite in the glass ceramic according to the invention is thus determined, for example, not only by the CaO and $SiO_2$ content in the starting glass or the heat treatment thereof but also by the manner of the activation due to the grinding of the starting glass.

In addition it was found that both the amount of precipitated wollastonite and the size of the wollastonite crystals have an influence on the translucence of the glass ceramic according to the invention. By means of a high wollastonite content or a crystallite size of more than 10 μm, strongly cloudy glass ceramics with a contrast value (CR value according to British Standard BS 5612) of more than 90 can be produced. These glass ceramics are suitable in particular for the preparation of a dental abutment structure or a dental superstructure to which a suitable veneer is applied.

On the other hand, translucent glass ceramics with a CR value of less than 75 can be produced at a low wollastonite content or a crystallite size of 5 to 10 μm. These glass ceramics are suitable in particular for the preparation of optically demanding dental restorations, such as crowns, veneers and inlays.

The glass ceramic according to the invention is further characterized in that, even after the final formation of the lithium disilicate crystal phase, which gives the glass ceramic a high strength, it can be easily machined in order to give it e.g. the shape of a dental restoration. This is a particular advantage over conventional lithium disilicate glass ceramics, in the case of which a precursor which can be machined more easily is often used and after the machining this precursor must be subjected to another heat treatment to form the desired lithium disilicate glass ceramic.

The glass ceramic according to the invention is also characterized by a very good chemical resistance. To determine the chemical resistance, the glass ceramic was tested according to ISO standard 6872 (2008) by determining the mass loss during storage in aqueous acetic acid. The glass ceramic according to the invention displayed a mass loss of preferably less than 100 μg/cm$^2$.

The glass ceramic according to the invention also has a biaxial breaking strength $\sigma_B$ of preferably at least 200 MPa and particularly preferably 250 to 350 MPa. The biaxial breaking strength was determined according to ISO 6872 (2008) (piston-on-three-ball test).

Therefore, the glass ceramic according to the invention offers a desirable combination of advantageous optical and mechanical properties, such as are sought in particular for a dental material.

The invention likewise relates to precursors with a corresponding composition from which the glass ceramic according to the invention can be prepared by heat treatment. These precursors are a starting glass with a corresponding composition and a starting glass with nuclei with a corresponding composition. The term "corresponding composition" means that these precursors comprise the same components in the same amounts as the glass ceramic, wherein the components are calculated as oxides, as is customary for glasses and glass ceramics.

The invention therefore also relates to a starting glass which comprises the components of the lithium silicate-wollastonite glass ceramic according to the invention. All those embodiments which are specified as preferred for the components of the lithium silicate-wollastonite glass ceramic according to the invention are also preferred for the components of the starting glass.

Particularly preferably the starting glass is present in ground form or in the form of a powder compact pressed from ground starting glass. In both of these forms the starting glass has undergone an activation by means of the grinding, which activation is required for the later crystallization of wollastonite.

Further, the invention also relates to a starting glass which comprises nuclei for the crystallization of lithium silicate and/or wollastonite.

The invention further relates to a process for the preparation of the lithium silicate-wollastonite glass ceramic according to the invention, in which
 (a) starting glass is ground,
 (b) optionally the ground starting glass is pressed to form a powder compact and
 (c) the ground starting glass or the powder compact is subjected to at least one heat treatment at a temperature in the range of 700° to 950° C. for a period of in particular 5 to 120 min.

In stage (a) the starting glass according to the invention is ground in order to activate it for the crystallization of wollastonite.

The grinding is carried out in particular in mills and preferably in ball mills, jet mills, such as opposed jet mills, or vibratory mills. The glass particles obtained after the grinding usually have an average particle size in the range of 10 to 30 µm, relative to the number of particles.

By using different grinding processes, e.g. by using different mills, a different degree of activation of the starting glass can be achieved and thus also the amount of wollastonite finally crystallized can be controlled.

The starting glass subjected to the grinding process is preferably present in the form of a granular material. The term "granular material" denotes a particulate starting glass. To produce particulate starting glass a melt of the starting glass can be poured into water and thus quenched. This process is also called fritting and the granular glass material obtained is called glass frits. A granular material can also be produced in another way, however, such as for example by quenching in a roller mill and subsequent comminution.

The preparation of the starting glass is carried out in particular such that a mixture of suitable starting materials, such as carbonates, oxides and phosphates, is melted at temperatures of in particular 1300 to 1700° C., preferably about 1500° C., for a period of 0.5 to 5 h.

In the optional stage (b) the ground starting glass is pressed to form a powder compact. It is preferred that this stage is carried out in the process according to the invention.

In contrast to a glass monolith, such as is obtained e.g. by pouring a glass melt into a mould, the powder compact according to the invention is characterized by a large inner surface area on which crystallization of wollastonite can take place.

The powder compact can have any desired geometry. Usually, the powder compact already substantially has the shape which is desired for a blank made of the glass ceramic according to the invention produced later.

In stage (c) the ground glass or the powder compact is subjected to at least one heat treatment. This at least one heat treatment takes place at a temperature in the range of 700° to 950° C., preferably 750° to 900° C., for a period of in particular 5 to 120 min, preferably 5 to 90 min.

The heat treatment is carried out until the desired amount of lithium silicate and wollastonite is crystallized and thus the lithium silicate-wollastonite glass ceramic according to the invention has been formed. The heat treatment can also take place in stages, wherein first of all a precursor, such as a nucleated starting glass, is formed by means of a first heat treatment and then the glass ceramic according to the invention is formed by means of a second heat treatment at a higher temperature. The formation of nuclei for the crystallization of lithium silicate usually takes place at a temperature in the range of 460 to 500° C.

It is further preferred to choose the heat treatment such that there is also an at least partial sintering, i.e. a presintering, of the ground starting glass or of the powder compact. It is particularly preferred if the heat treatment also leads to as complete a sintering as possible, i.e. to a dense sintering of the ground starting glass or of the powder compact.

Densely-sintered glass ceramics produced from ground starting glass are used above all as coatings on substrates such as dental superstructures. Densely-sintered glass ceramics produced from powder compacts are used above all as blanks from which dental restorations such as bridges, crowns, inlays or onlays can be prepared using suitable moulding processes such as pressing and in particular machining.

After completion of stage (c) the lithium silicate-wollastonite glass ceramic according to the invention is present.

Dental restorations, such as bridges, inlays, onlays, crowns, veneers, facets or abutments, can be prepared from the glass ceramic according to the invention and the glasses according to the invention. The invention therefore relates to the use thereof as dental material and in particular to the use thereof for the preparation of dental restorations. It is preferred that the glass ceramic or the glass is given the shape of the desired dental restoration by pressing or machining.

The pressing is usually carried out under increased pressure and at increased temperature. It is preferred that the pressing is carried out at a temperature of 700 to 1200° C. It is further preferred to carry out the pressing at a pressure of 10 to 30 bar. During pressing, the desired change in shape is achieved by viscous flow of the material used. The glasses and glass ceramics according to the invention can in particular be used in the form of blanks in any shape and size. For the pressing, the glass ceramic according to the invention is preferably used. Particularly preferably the glass ceramic according to the invention with lithium silicate and in particular with lithium disilicate as main crystal phase is used.

The machining is usually carried out by material removal processes and in particular by grinding and/or milling. It is particularly preferred that the machining is carried out as part of a CAD/CAM process. The glasses and glass ceramics according to the invention can be used in particular in the form of blanks. These are routinely adapted in terms of their shape to the type of machine used for the machining. The glass ceramic according to the invention is in particular used for the machining. Particularly preferably the glass ceramic according to the invention with lithium silicate and in particular with lithium disilicate as main crystal phase is used.

Because of the above-described properties of the glass ceramics according to the invention and the glasses according to the invention, these are suitable in particular for use in dentistry. A subject of the invention is therefore also the use of the glass ceramics according to the invention or the glasses according to the invention as dental material and in particular for the preparation of dental restorations such as crowns, bridges and abutments.

The invention therefore also relates to a process for the preparation of a dental restoration, in particular bridge, inlay, onlay, veneer, abutment, partial crown, crown or facet, in which the glass ceramic according to the invention or the glass according to the invention is given the shape of the desired dental restoration by pressing or by machining, in particular as part of a CAD/CAM process.

The invention is explained in more detail below with reference to non-limiting examples.

EXAMPLES

Examples 1 to 32—Composition and Crystal Phases

In total, 32 glasses and glass ceramics with the composition specified in Table I were prepared.

The following meanings apply in Table I:

$T_g$ glass transition temperature, determined by means of DSC $T_S$ and $t_S$ temperature and time used for melting the starting glass $T_{Kb}$ and $t_{Kb}$ temperature and time used for nucleation of the starting glass $T_{Sinter}$ and $t_{Sinter}$ temperature and time used for the heat treatment for the crystallization and sintering of compacts $T_{press}$ and $t_{press}$ temperature and holding time at temperature used for pressing crystallized compacts CR value contrast value of the glass ceramic according to British Standard BS 5612

$Li_2Si_2O_5$ lithium disilicate $Li_2SiO_3$ lithium metasilicate $CaSiO_3$ wollastonite KM ground with ball mill AFG ground with jet mill In Examples 1 to 32 glasses made of usual raw materials were melted in a platinum crucible at the temperature $T_S$ for a period $t_S$. Glass frits, i.e. granular glass material, were prepared by pouring the melted starting glasses into water. The three process variants A), B) and C) indicated below were used for the further processing of the glass frits into glass ceramics according to the invention.

It was shown that, depending on the $P_2O_5$ content, the lithium disilicate crystals obtained had a size of about 500 nm to 6 μm. The lithium disilicate crystals formed a cross-linked and interlocked structure, which is presumably also responsible for the good mechanical properties of the glass ceramics. The wollastonite crystals were present scattered in the lithium disilicate structure and had a size of about 5 μm to more than 10 μm.

A) Vibratory Mills

The glass frits prepared according to Examples 1 to 30 were ground with a KM100 vibratory mill from Retsch GmbH, Haan, Germany, or an RM31 zirconium oxide vibratory mill from Retsch GmbH, Haan, Germany, to an average particle size of <90 μm, relative to the number of particles. The ground glass powder was then pressed uniaxially to form a small cylinder and crystallized and sintered in a Programat-type furnace (Ivoclar Vivadent AG) at the temperature $T_{Sinter}$ for the period $t_{Sinter}$. X-ray diffraction analyses to determine the crystal phases present as well as colour measurements were carried out on the prepared test pieces.

B) Jet Mill

The glass frit with the composition according to Example 31 was ground in an AFG 100 opposed jet mill from Hosokawa Alpine to an average particle size of 23 μm, relative to the number of particles. The ground glass powder was then pressed uniaxially and crystallized and sintered in a Programat-type furnace (Ivoclar Vivadent AG) at the temperature $T_{Sinter}$ for the period $t_{Sinter}$. X-ray diffraction analyses were carried out on the test pieces prepared in this way.

C) Ball Mill

The glass frits with the composition according to Example 31 and 32 were ground in a ball mill to an average particle size of 23 μm, relative to the number of particles. The ball mill had, as grinding chamber, a cylindrical porcelain container with a volumetric capacity of 5 l. The following mixture of porcelain grinding balls was used as grinding medium: 0.9 kg with diameter 10 mm, 1.8 kg with diameter 20 mm and 0.9 kg with diameter 30 mm. The ground glass powders were then pressed uniaxially and crystallized and sintered in a Programat-type furnace (Ivoclar Vivadent AG) at the temperature $T_{Sinter}$ for the period $t_{Sinter}$. X-ray diffraction analyses were carried out on the test pieces prepared in this way to determine the crystal phases. The content of wollastonite crystals in these glass ceramics was higher than in the glass ceramics prepared according to variants A) and B).

TABLE 1

| Composition | 1 wt.-% | 2 wt.-% | 3 wt.-% | 4 wt.-% | 5 wt.-% | 6 wt.-% |
|---|---|---|---|---|---|---|
| $SiO_2$ | 62.4 | 68.2 | 64.5 | 63.3 | 63.4 | 63.2 |
| $Li_2O$ | 13.0 | 14.1 | 13.4 | 13.2 | 13.2 | 13.1 |
| CaO | 15.4 | 7.7 | 10.0 | 9.8 | 9.9 | 9.8 |
| MgO | — | — | — | — | — | — |
| SrO | — | — | — | — | — | — |
| ZnO | — | — | — | — | — | — |
| $Na_2O$ | — | — | — | — | — | — |
| $K_2O$ | 3.4 | 3.7 | 3.5 | 3.4 | 3.4 | 3.4 |
| $Cs_2O$ | — | — | — | — | — | — |
| $Rb_2O$ | — | — | — | — | — | — |
| $Al_2O_3$ | 3.0 | 3.2 | 3.1 | 3.0 | 3.0 | 3.0 |
| $B_2O_3$ | — | — | — | — | — | — |
| $Y_2O_3$ | — | — | — | — | — | — |
| $La_2O_3$ | — | — | — | — | — | — |
| $ZrO_2$ | — | — | — | — | — | — |
| $P_2O_5$ | 2.8 | 3.1 | 5.5 | 5.4 | 5.4 | 5.4 |
| $GeO_2$ | — | — | — | — | — | — |
| $CeO_2$ | — | — | — | 1.7 | 1.2 | 1.2 |
| $V_2O_5$ | — | — | — | 0.2 | 0.2 | 0.2 |
| $Er_2O_3$ | — | — | — | — | 0.3 | 0.7 |
| $TiO_2$ | — | — | — | — | — | — |
| $SnO_2$ | — | — | — | — | — | — |
| $Nb_2O_5$ | — | — | — | — | — | — |
| $Ta_2O_5$ | — | — | — | — | — | — |
| $MoO_3$ | — | — | — | — | — | — |
| $WO_3$ | — | — | — | — | — | — |
| $T_g$/° C. | 472.3 | 464.1 | 466.3 | 466.9 | 467.5 | 468.5 |
| $T_{Kb}$/° C., $t_{Kb}$/min. | 480, 20 | 480, 20 | 490, 20 | 490, 20 | 490, 20 | 490, 20 |
| $T_s$/° C., $t_s$/min. | 1500, 60 | 1500, 120 | 1500, 90 | 1500, 90 | 1500, 90 | 1500, 90 |
| Main crystal phase | $Li_2SiO_3$ | $Li_2Si_2O_5$ | $Li_2Si_2O_5$ | $Li_2Si_2O_5$ | $Li_2Si_2O_5$ | $Li_2Si_2O_5$ |

TABLE 1-continued

| | | | | | | |
|---|---|---|---|---|---|---|
| Further crystal phases | $CaSiO_3$, $Li_3PO_4$ | $Li_2SiO_3$, $Li_3PO_4$, $CaSiO_3$ | $Li_3PO_4$, $CaSiO_3$ | $Li_3PO_4$, $CaSiO_3$ | $Li_3PO_4$, $CaSiO_3$ | $Li_3PO_4$, $CaSiO_3$ |
| $T_{Sinter}$/° C., $t_{Sinter}$/min. $T_{press}$/° C., $t_{press}$/min. | 850, 5 | 850, 30 | 810, 5 | 830, 30 | 810, 10 | 810, 30 |

| | Example No. | | | | | |
|---|---|---|---|---|---|---|
| Composition | 7 wt.-% | 8 wt.-% | 9 wt.-% | 10 wt.-% | 11 wt.-% | 12 wt.-% |
| $SiO_2$ | 64.1 | 60.7 | 67.2 | 65.8 | 63.1 | 60.8 |
| $Li_2O$ | 13.3 | 16.5 | 13.9 | 13.7 | 13.1 | 12.7 |
| CaO | 10.0 | 10.3 | 10.2 | 10.1 | 9.9 | 9.5 |
| MgO | — | — | — | — | — | — |
| SrO | — | — | — | — | — | — |
| ZnO | — | — | — | — | — | — |
| $Na_2O$ | — | — | — | — | — | 5.6 |
| $K_2O$ | 3.5 | 3.6 | — | 3.5 | 3.5 | 3.3 |
| $Cs_2O$ | — | — | — | — | — | — |
| $Rb_2O$ | — | — | — | — | — | — |
| $Al_2O_3$ | 3.1 | 3.2 | 3.1 | 1.3 | 4.9 | 2.9 |
| $B_2O_3$ | — | — | — | — | — | — |
| $Y_2O_3$ | — | — | — | — | — | — |
| $La_2O_3$ | — | — | — | — | — | — |
| $ZrO_2$ | — | — | — | — | — | — |
| $P_2O_5$ | 6.0 | 5.7 | 5.6 | 5.6 | 5.5 | 5.2 |
| $GeO_2$ | — | — | — | — | — | — |
| $CeO_2$ | — | — | — | — | — | — |
| $V_2O_5$ | — | — | — | — | — | — |
| $Er_2O_3$ | — | — | — | — | — | — |
| $TiO_2$ | — | — | — | — | — | — |
| $SnO_2$ | — | — | — | — | — | — |
| $Nb_2O_5$ | — | — | — | — | — | — |
| $Ta_2O_5$ | — | — | — | — | — | — |
| $MoO_3$ | — | — | — | — | — | — |
| $WO_3$ | — | — | — | — | — | — |
| $T_g$/° C. | 466.4 | 450.8 | 467.9 | 461.9 | 462.7 | 436.8 |
| $T_{Kb}$/° C., $t_{Kb}$/min. | 490, 20 | 470, 20 | 490, 20 | 480, 20 | 480, 20 | 460, 20 |
| $T_s$/° C., $t_s$/min. | 1500, 60 | 1500, 90 | 1500, 90 | 1500, 90 | 1500, 90 | 1500, 120 |
| Main crystal phase | $Li_2Si_2O_5$ | $Li_2SiO_3$ | $Li_2Si_2O_5$ | $Li_2Si_2O_5$ | $Li_2Si_2O_5$ | $Li_2SiO_3$ |
| Further crystal phases | $Li_3PO_4$, $CaSiO_3$ | $Li_3PO_4$, $CaSiO_3$ | $Li_3PO_4$, $CaSiO_3$, $LiAlSi_2O_6$, $SiO_2$ | $Li_3PO_4$, $CaSiO_3$ | $Li_2SiO_3$ $Li_3PO_4$, $CaSiO_3$ | $Li_3PO_4$, $CaSiO_3$ |
| $T_{Sinter}$/° C., $t_{Sinter}$/min. $T_{press}$/° C., $t_{press}$/min. | 850, 5 | 850, 5 | 880, 5 | 850, 30 | 800, 30 | 800, 30 |

| | Example No. | | | | | |
|---|---|---|---|---|---|---|
| Composition | 13 wt.-% | 14 wt.-% | 15 wt.-% | 16 wt.-% | 17 wt.-% | 18 wt.-% |
| $SiO_2$ | 56.9 | 63.3 | 61.5 | 62.1 | 62.5 | 61.8 |
| $Li_2O$ | 11.9 | 13.2 | 12.8 | 12.9 | 13.0 | 12.9 |
| CaO | 8.9 | 9.9 | 9.6 | 9.7 | 9.7 | 9.6 |
| MgO | — | 1.8 | — | — | — | — |
| SrO | — | — | 4.6 | — | — | — |
| ZnO | — | — | — | 3.6 | — | — |
| $Na_2O$ | — | — | — | — | — | — |
| $K_2O$ | 3.1 | 3.4 | 3.3 | 3.4 | 3.4 | 3.4 |
| $Cs_2O$ | 11.6 | — | — | — | — | — |
| $Rb_2O$ | — | — | — | — | — | — |
| $Al_2O_3$ | 2.7 | 3.0 | 2.9 | 3.0 | 3.0 | 3.0 |
| $B_2O_3$ | — | — | — | — | 3.1 | — |
| $Y_2O_3$ | — | — | — | — | — | 4.0 |
| $La_2O_3$ | — | — | — | — | — | — |
| $ZrO_2$ | — | — | — | — | — | — |
| $P_2O_5$ | 4.9 | 5.4 | 5.3 | 5.3 | 5.3 | 5.3 |
| $GeO_2$ | — | — | — | — | — | — |
| $CeO_2$ | — | — | — | — | — | — |
| $V_2O_5$ | — | — | — | — | — | — |
| $Er_2O_3$ | — | — | — | — | — | — |
| $TiO_2$ | — | — | — | — | — | — |
| $SnO_2$ | — | — | — | — | — | — |
| $Nb_2O_5$ | — | — | — | — | — | — |
| $Ta_2O_5$ | — | — | — | — | — | — |
| $MoO_3$ | — | — | — | — | — | — |
| $WO_3$ | — | — | — | — | — | — |
| $T_g$/° C. | 473.8 | 462 | 461.3 | 463.1 | 468.6 | 474.7 |

TABLE 1-continued

| | | | | | | |
|---|---|---|---|---|---|---|
| $T_{Kb}$/° C., $t_{Kb}$/min. | 490, 20 | 490, 20 | 480, 20 | 460, 20 | 470, 20 | 470, 20 |
| $T_s$/° C., $t_s$/min. | 1500, 90 | 1500, 90 | 1500, 90 | 1500, 120 | 1500, 120 | 1500, 90 |
| Main crystal phase | $Li_2SiO_3$ | $Li_2Si_2O_5$ | $Li_2Si_2O_5$ | $Li_2Si_2O_5$ | $Li_2Si_2O_5$ | $Li_2Si_2O_5$ |
| Further crystal phases | $Li_3PO_4$, $CaSiO_3$, $CsAlSi_5O_{12}$ | $Li_2SiO_3$, $Li_3PO_4$, $CaSiO_3$ | $Li_2SiO_3$, $Li_3PO_4$, $CaSiO_3$ | $Li_2SiO_3$, $Li_3PO_4$, $CaSiO_3$ | $Li_3PO_4$, $CaSiO_3$ | $Li_2SiO_3$, $Li_3PO_4$, $CaSiO_3$, $Y_2O_3$ |
| $T_{Sinter}$/° C., $t_{Sinter}$/min. | 820, 30 | 810, 30 | 810, 30 | 810, 30 | 810, 30 | 810, 30 |
| $T_{press}$/° C., $t_{press}$/min. | | | | | | |

| | Example No. | | | | | |
|---|---|---|---|---|---|---|
| Composition | 19 wt.-% | 20 wt.-% | 21 wt.-% | 22 wt.-% | 23 wt.-% | 24 wt.-% |
| $SiO_2$ | 61.5 | 60.2 | 62.1 | 61.0 | 62.4 | 61.5 |
| $Li_2O$ | 12.8 | 12.5 | 12.9 | 12.7 | 13.0 | 12.8 |
| CaO | 9.6 | 9.4 | 9.7 | 9.5 | 9.7 | 9.6 |
| MgO | — | — | — | — | — | — |
| SrO | — | — | — | — | — | — |
| ZnO | — | — | — | — | — | — |
| $Na_2O$ | — | — | — | — | — | — |
| $K_2O$ | 3.3 | 3.3 | 3.4 | 3.3 | 3.4 | 3.3 |
| $Cs_2O$ | — | — | — | — | — | — |
| $Rb_2O$ | — | — | — | — | — | — |
| $Al_2O_3$ | 2.9 | 2.9 | 3.0 | 2.9 | 3.0 | 2.9 |
| $B_2O_3$ | — | — | — | — | — | — |
| $Y_2O_3$ | — | — | — | — | — | — |
| $La_2O_3$ | — | — | — | — | — | — |
| $ZrO_2$ | — | — | — | 5.4 | — | — |
| $P_2O_5$ | 5.3 | 5.2 | 5.3 | 5.2 | 5.3 | 5.3 |
| $GeO_2$ | 4.6 | — | — | — | — | — |
| $CeO_2$ | — | — | — | — | — | — |
| $V_2O_5$ | — | — | — | — | 3.2 | — |
| $Er_2O_3$ | — | — | — | — | — | — |
| $TiO_2$ | — | — | 3.6 | — | — | — |
| $SnO_2$ | — | 6.5 | — | — | — | — |
| $Nb_2O_5$ | — | — | — | — | — | 4.6 |
| $Ta_2O_5$ | — | — | — | — | — | — |
| $MoO_3$ | — | — | — | — | — | — |
| $WO_3$ | — | — | — | — | — | — |
| $T_g$/° C. | 466.8 | 487.9 | 471.8 | 479.3 | 455.8 | 472.1 |
| $T_{Kb}$/° C., $t_{Kb}$/min. | 470, 20 | 460, 20 | 470, 20 | 480, 20 | 480, 20 | 490, 20 |
| $T_s$/° C., $t_s$/min. | 1500, 60 | 1500, 60 | 1500, 60 | 1500, 60 | 1500, 60 | 1500, 60 |
| Main crystal phase | $Li_2Si_2O_5$ | $Li_2Si_2O_5$ | $Li_2Si_2O_5$ | $Li_2Si_2O_5$ | $Li_2Si_2O_5$ | $Li_2Si_2O_5$ |
| Further crystal phases | $Li_3PO_4$, $CaSiO_3$ | $Li_2SiO_3$, $Li_3PO_4$, $CaSiO_3$, $SnO_2$ | $Li_2SiO_3$, $Li_3PO_4$,, $CaSiO_3$ | $Li_2SiO_3$, $Li_3PO_4$, $CaSiO_3$ | $Li_3PO_4$, $CaSiO_3$ | $Li_3PO_4$, $CaSiO_3$ |
| $T_{Sinter}$/° C., $t_{Sinter}$/min. | 800, 30 | 810, 60 | 800, 30 | 810, 60 | 790, 30 | 790, 60 |
| $T_{press}$/° C., $t_{press}$/min. | | | | | | |

| | Example No. | | | | | |
|---|---|---|---|---|---|---|
| Composition | 25 wt.-% | 26 wt.-% | 27 wt.-% | 28 wt.-% | 29 wt.-% | 30 wt.-% |
| $SiO_2$ | 62.7 | 61.8 | 67.5 | 61.9 | 72.7 | 70.9 |
| $Li_2O$ | 13.1 | 12.9 | 14.0 | 12.9 | 12.9 | 12.8 |
| CaO | 9.8 | 9.6 | 7.6 | 9.6 | 7.7 | 7.7 |
| MgO | — | — | — | — | — | — |
| SrO | — | — | — | — | — | — |
| ZnO | — | — | — | — | — | — |
| $Na_2O$ | — | — | — | — | — | — |
| $K_2O$ | 3.4 | 3.4 | 1.6 | 3.4 | 1.0 | 0.9 |
| $Cs_2O$ | — | — | — | — | — | — |
| $Rb_2O$ | — | — | — | — | — | — |
| $Al_2O_3$ | 3.0 | 2.9 | 1.8 | 3.0 | 3.3 | 5.4 |
| $B_2O_3$ | — | — | — | — | — | — |
| $Y_2O_3$ | — | — | — | — | — | — |
| $La_2O_3$ | — | — | 4.4 | — | — | — |
| $ZrO_2$ | — | — | — | — | — | — |
| $P_2O_5$ | 5.4 | 5.3 | 3.1 | 5.3 | 2.4 | 2.3 |
| $GeO_2$ | — | — | — | — | — | — |
| $CeO_2$ | — | — | — | — | — | — |
| $V_2O_5$ | — | — | — | — | — | — |
| $Er_2O_3$ | — | — | — | — | — | — |
| $TiO_2$ | — | — | — | — | — | — |
| $SnO_2$ | — | — | — | — | — | — |
| $Nb_2O_5$ | — | — | — | — | — | — |

TABLE 1-continued

| | | | | | | |
|---|---|---|---|---|---|---|
| Ta$_2$O$_5$ | — | — | — | 3.9 | — | — |
| MoO$_3$ | 2.6 | — | — | — | — | — |
| WO$_3$ | — | 4.1 | — | — | — | — |
| T$_g$/° C. | 466.7 | 469.6 | 465.3 | 470.8 | 470.7 | 473.8 |
| T$_{Kb}$/° C., t$_{Kb}$/min. | 490, 20 | 490, 20 | 490, 20 | 490, 20 | 480, 20 | 490, 20 |
| T$_s$/° C., t$_s$/min. | 1500, 60 | 1500, 60 | 1500, 90 | 1500, 90 | 1500, 90 | 1500, 90 |
| Main crystal phase | Li$_2$Si$_2$O$_5$ | Li$_2$Si$_2$O$_5$ | Li$_2$Si$_2$O$_5$ | Li$_2$Si$_2$O$_5$ | Li$_2$Si$_2$O$_5$ | Li$_2$Si$_2$O$_5$ |
| Further crystal phases | Li$_3$PO$_4$, CaSiO$_3$ | Li$_3$PO$_4$, CaSiO$_3$, CaWO$_4$ | Li$_3$PO$_4$, CaSiO$_3$ | Li$_3$PO$_4$, CaSiO$_3$ | Li$_3$PO$_4$, CaSiO$_3$, SiO$_2$, Li$_x$Al$_x$Si$_{1-x}$O$_2$ | Li$_3$PO$_4$, CaSiO$_3$, LiAlSi$_3$O$_8$ |
| T$_{Sinter}$/° C., t$_{Sinter}$/min. | 810, 30 | 810, 30 | 850, 30 | 810, 30 | 870, 5 | 870, 5 |
| T$_{press}$/° C., t$_{press}$/min. | | | | | | |

| | Example No. | |
|---|---|---|
| Composition | 31 wt.-% | 32 wt.-% |
| SiO$_2$ | 66.1 | 68.1 |
| Li$_2$O | 13.8 | 14.1 |
| CaO | 7.6 | 5.1 |
| MgO | — | — |
| SrO | — | — |
| ZnO | — | — |
| Na$_2$O | — | — |
| K$_2$O | 3.6 | 3.7 |
| Cs$_2$O | — | — |
| Rb$_2$O | — | — |
| Al$_2$O$_3$ | 3.2 | 3.2 |
| B$_2$O$_3$ | — | — |
| Y$_2$O$_3$ | — | — |
| La$_2$O$_3$ | — | — |
| ZrO$_2$ | — | — |
| P$_2$O$_5$ | 5.7 | 5.8 |
| GeO$_2$ | — | — |
| CeO$_2$ | — | — |
| V$_2$O$_5$ | — | — |
| Er$_2$O$_3$ | — | — |
| TiO$_2$ | — | — |
| SnO$_2$ | — | — |
| Nb$_2$O$_5$ | — | — |
| Ta$_2$O$_5$ | — | — |
| MoO$_3$ | — | — |
| WO$_3$ | — | — |
| T$_g$/° C. | 471.3 (KM)/469.8 (AFG) | 467.8 (KM) |
| T$_{Kb}$/° C., t$_{Kb}$/min. | 500, 20 (KM)/(AFG) | 500, 20 (KM) |
| T$_s$/° C., t$_s$/min. | 1500, 120 | 1500, 120 |
| Main crystal phase | Li$_2$Si$_2$O$_5$ | Li$_2$Si$_2$O$_5$ |
| Further crystal phases | Li$_3$PO$_4$, CaSiO$_3$ | Li$_3$PO$_4$, CaSiO$_3$, SiO$_2$ |
| T$_{Sinter}$/° C., t$_{Sinter}$/min. | 800, 5 (KM); 800, 20 (AFG) | 850, 10 (KM) |
| T$_{press}$/° C., t$_{press}$/min. | 900/25 | |

Example 33—Hot Pressing

A glass with the composition according to Example 31 was melted in a platinum crucible at a temperature of 1500° C. and then poured into water. The glass frits prepared in this way were ground with an AFG 100 opposed jet mill from Hosokawa Alpine to an average particle size of 23 μm, relative to the number of particles. A powder compact was prepared by uniaxial pressing from the glass powder obtained. The press blank was densely sintered at a temperature of 800° C. and a holding time of 20 min in a Programat-type furnace. The densely sintered and already crystallized blank was then pressed by means of hot pressing at a temperature of 900° C. with a holding time of 25 min. The pressed test piece had a CR value of 86.65 and a coefficient of thermal expansion of $10.75 \times 10^{-6}$ K$^{-1}$, measured in the range of 100 to 500° C.

Example 34—Machinability

To test the machinability, glass powders according to Examples 3, 5 and 31 were pressed uniaxially to form blocks and densely sintered in a Programat-type furnace. Corresponding holders were then glued to the glass ceramic blocks prepared in this way and they were processed with a CAD/CAM grinding unit (Sirona InLab). To test the processability, biaxial test pieces were ground out of the blocks, which was possible without problems and only with low tool wear.

The invention claimed is:

1. Lithium silicate-wollastonite glass ceramic, which comprises 1.0 to 7.0 wt.-% P$_2$O$_3$ and comprises lithium silicate as a crystal phase and wollastonite as a further crystal phase.

2. Glass ceramic according to claim 1, which comprises 55.0 to 74.0 wt.-% SiO$_2$.

3. Glass ceramic according to claim 1, which comprises 10.0 to 18.0 wt.-% Li$_2$O.

4. Glass ceramic according to claim 1, which comprises 4.0 to 17.0 wt.-% CaO.

5. Glass ceramic according to claim 1, which comprises 0.5 to 6.0 wt.-% Al$_2$O$_3$.

6. Glass ceramic according to claim 1, which comprises 0 to 5.0 wt.-% $K_2O$.

7. Glass ceramic according to claim 1, which comprises 2.0 to 6.0 wt.-% $P_2O_3$.

8. Glass ceramic according to claim 1, which comprises 0 to 13.0 wt.-% further alkali metal oxide $Me^I_2O$, wherein $Me^I_2O$ is selected from $Na_2O$, $Rb_2O$ and/or $Cs_2O$.

9. Glass ceramic according to claim 1, which comprises 0 to 6.0 wt.-% further oxide of divalent elements $Me^{II}O$, wherein $Me^{II}O$ is selected from MgO, SrO and/or ZnO.

10. Glass ceramic according to claim 1, which comprises 0 to 6.0 wt.-% oxide of trivalent elements $Me^{III}_2O_3$, wherein $Me^{III}_2O_3$ is selected from $B_2O_3$, $Y_2O_3$, $La_2O_3$ and/or $Er_2O_3$.

11. Glass ceramic according to claim 1, which comprises 0 to 8.0 wt.-% further oxide of tetravalent elements $Me^{IV}O_2$, wherein $Me^{IV}O_2$ is selected from $ZrO_2$, $GeO_2$, $CeO_2$, $TiO_2$ and/or $SnO_2$.

12. Glass ceramic according to claim 1, which comprises 0 to 6.0 wt.-% further oxide of pentavalent elements $Me^V_2O_5$, wherein $Me^V_2O_5$ is selected from $V_2O_5$, $Ta_2O_5$ and/or $Nb_2O_5$.

13. Glass ceramic according to claim 1, which comprises 0 to 6.0 wt.-% oxide of hexavalent elements $Me^{VI}O_3$, wherein $Me^{VI}O_3$ is selected from $WO_3$ and/or $MoO_3$.

14. Glass ceramic according to claim 1, which comprises at least one of the following components in the amounts specified:

| Component | wt.-% |
| --- | --- |
| $SiO_2$ | 56.0 to 74.0 |
| $Li_2O$ | 10.0 to 18.0 |
| CaO | 4.0 to 17.0 |
| $Al_2O_3$ | 0.5 to 6.0 |
| $K_2O$ | 0 to 5.0 |
| $P_2O_5$ | 1.0 to 7.0 |
| $Me^I_2O$ | 0 to 13.0 |
| $Me^{II}O$ | 0 to 6.0 |
| $Me^{III}_2O_3$ | 0 to 6.0 |
| $Me^{IV}O_2$ | 0 to 8.0 |
| $Me^V_2O_5$ | 0 to 6.0 |
| $Me^{VI}O_3$ | 0 to 6.0. |

15. Glass ceramic according to claim 1, which comprises lithium disilicate and/or lithium metasilicate.

16. Glass ceramic according to claim 1, which comprises lithium metasilicate or lithium disilicate as main crystal phase.

17. Lithium silicate-wollastonite glass ceramic, which comprises lithium silicate as a crystal phase and wollastonite and lithium phosphate as further crystal phases.

18. Glass ceramic according to claim 1, which is present in the form of a blank or a dental restoration.

19. Starting glass, which comprises 1.0 to 7.0 wt.-% $P_2O_5$ and comprises nuclei for the crystallization of lithium silicate as a crystal phase and wollastonite as a further crystal phase.

20. Starting glass according to claim 19, which is present in the form of a ground powder or a compact made of ground powder.

21. Process for the preparation of the glass ceramic according to claim 1, in which (a) a starting glass which comprises 1.0 to 7.0 wt.-% $P_2O_5$ and comprises nuclei for the crystallization of lithium silicate and/or wollastonite is ground, (b) optionally the ground starting glass is pressed to form a powder compact and (c) the ground starting glass or the powder compact is subjected to at least one heat treatment at a temperature in the range of 700° to 950° C. for a period of 5 to 120 min.

22. Process for the preparation of a dental restoration comprising a bridge, inlay, onlay, veneer, abutment, partial crown, crown or facet, in which a lithium silicate-wollastonite glass ceramic, which comprises lithium silicate as a crystal phase and wollastonite as a further crystal phase, is given the shape of the desired dental restoration by pressing or machining.

* * * * *